United States Patent [19]

Han et al.

[11] 3,937,845

[45] Feb. 10, 1976

[54] SEMI-SOLID FERMENTATION OF STRAW

[75] Inventors: Youn W. Han; Arthur W. Anderson, both of Corvallis, Oreg.

[73] Assignee: The United States of America as represented by the Secretary of Agriculture, Washington, D.C.

[22] Filed: Jan. 8, 1975

[21] Appl. No.: 539,552

[52] U.S. Cl. .................... 426/53; 426/69; 426/807
[51] Int. Cl.² ........................................ A23K 1/00
[58] Field of Search ............ 426/52, 49, 2, 807, 53, 426/54, 372–374, 69, 18, 210, 615, 626; 195/31, 33, 82

[56] References Cited
UNITED STATES PATENTS

| | | | |
|---|---|---|---|
| 1,807,067 | 5/1931 | Mabee | 426/53 |
| 3,251,716 | 5/1966 | Porter | 426/373 X |
| 3,616,222 | 10/1971 | Dasinger | 195/33 X |
| 3,751,338 | 8/1973 | Farris | 195/82 |
| 3,769,170 | 10/1973 | Kondo | 195/82 |

*Primary Examiner*—A. Louis Monacell
*Assistant Examiner*—R. B. Penland
*Attorney, Agent, or Firm*—M. Howard Silverstein; W. Takacs; Max D. Hensley

[57] ABSTRACT

The digestibility and protein content of straw is enhanced by treating it with dilute acid, ammoniating the acid-treated straw, and fermenting it with a yeast such as *Candida utilis*. The so-treated straw is useful as a feed for ruminants and other animals.

6 Claims, No Drawings

SEMI-SOLID FERMENTATION OF STRAW

DESCRIPTION OF THE INVENTION

The invention relates to and has among its objects the provision of novel processes for increasing the digestibility and protein content of straw whereby to provide nutritious animal feeds. Further objects of the invention will be evident from the following description wherein parts and percentages are by weight unless otherwise specified.

Over 200 million tons of cellulosic agricultural wastes are produced each year in the U.S. Naturally, the disposal of such a large quantity presents problems. Much of this waste is disposed of by burning, but such method has been increasingly under criticism because of the air pollution that results. Many cities and states have totally or partially banned the open burning of straw and similar cellulosic agricultural wastes.

Straw contains components such as cellulose and hemicellulose which could make it desirable as an animal feed, especially for ruminants. Unfortunately, its low digestibility and low protein content presently prevent its use in feedlots.

Various methods have been advocated for enhancing the digestibility or the nutritive value of straw. For example, digestibility can be increased by treating the straw with sodium hydroxide. The nutritive value of straw can be supplemented by adding thereto a non-protein nitrogen source. In addition, efforts have been made to produce high-protein feeds by applying submerged microbial fermentation to cellulosic substrates. The above methods, however, have disadvantages either because they are too expensive or because they do not yield products of acceptable food value and digestibility, or both.

The invention described herein provides means for obviating the problems outlined above. By application of the processes of the invention straw is converted into products which exhibit substantial increases in both digestibility and protein content. In addition, the processes of the invention are simple and do not require any elaborate equipment or expensive reagents so that economic advantages are gained.

In general, according to the invention, straw is first treated with dilute acid. The acid-treated straw is ammoniated and then fermented with a yeast or other microorganism.

The invention is of wide versatility and may be applied to straws of cereal grains, such as rice, wheat, oats, barley, rye, etc. and those of grasses such as orchard green, bent, red fescue, Kentucky blue, rye grass (annual or perennial), etc. The digestibility and protein value of agricultural wastes such as leaves and stems may also be enhanced by the processes of the invention.

DETAILED DESCRIPTION OF THE INVENTION

In a practice of the invention, straw—preferably in comminuted form such as chopped or ground—is first hydrolyzed by treatment with dilute sulphuric acid. This is accomplished by mixing the straw (1 part) with about 2 to 4 parts of aqueous sulphuric acid having a normality of about 0.1 to 1, and holding the mixture at about 100° to 125° C. for about 30 to 60 minutes. It is, of course, obvious that at the higher temperatures in the said range—i.e., above 100° C.—the reaction is carried out in pressure-resistant equipment. In addition, it should be noted that the higher the temperature, the less concentrated the acid need be to attain the desired result. In a preferred embodiment of the invention, one part of straw is treated with 3 parts of 0.5 N sulphuric acid at 121° C. for 30 minutes. The acid treatment in accordance with the invention primarily causes the hemicellulose content of the straw to be converted into monomeric sugars such as xylose, glucose, mannose, arabinose, and galactose. In a later stage of the process of the invention, these sugars are utilized as a carbon source for the growth of yeast or other microorganism.

After completion of the acid treatment, the resulting mass is adjusted to a pH of 4.0–4.5 by addition of ammonia or ammonium hydroxide. This partial neutralization step provides the appropriate pH for microbial growth in a subsequent step, and also provides a nitrogen source required for the growth of the microorganism.

Next, the ammoniated mass is inoculated with a yeast or other microorganism and fermented under aerobic conditions. Typical microorganisms useful in the process of the invention are *Candida utilis*, *Pullularia* (*Aureobasidium*) *pullulans*, and *Trichoderma viride*. Generally, the fermentation is conducted at a temperature of about 25°–30° C. for a period of 1 to 7 days. Preferably, some means of agitation should be applied to the fermenting mass, such as stirring, shaking, tumbling, or the like so that the mass will be properly aerated.

The inoculation may be with a pure culture of the selected microorganism or it may be with a portion of straw material which had previously been fermented in accordance with the invention. Thus in operating the process in a continuous fashion, a small portion of fermented straw may be recycled and used as the inoculum for the next succeeding fermentation.

Following completion of the fermentation, the mass is dried, for example, by conventional hot air dehydration. Products of the invention exhibit a 3- to 4-fold increase in protein content. In addition, digestibility is increased by 40% or more.

The process of the invention may be carried out batch-wise or continuously. For example, the fermentation step can be carried out in a continuous manner by providing a conveyor which carried the fermenting mass through a chamber equipped with temperature control, ventilation means, and means to tumble or otherwise agitate the mass. Other methods of continuous operation will be obvious to those skilled in the art.

An advantage of the invention is that it renders unnecessary the elaborate controls and procedures required in submerged liquid fermentations. For example, in accordance with the invention the substrate under fermentation is a moist fibrous mass containing about 20–33% solids and 80–67% water. It is pervious to air so that it can be effectively aerated by simple tumbling, shaking, or stirring. The use of spargers, pumps, and the like required in submerged liquid fermentations are not needed. Also, in accordance with the invention the various conditions of pH, temperature, and the like need not be rigorously controlled. Thus the elaborate control mechanisms required with submerged liquid fermentations are unnecessary. Foaming problems frequently encountered in submerged liquid fermentations do not occur in the process of the invention. Another advantage of the invention is that it yields a product which in its entirety is useful as an animal feed. This is in contrast to systems of submerged liquid fermentation where the products must be harvested from the fermentation broth by centrifugation or other costly procedure.

A basic advantage of the invention is that we utilize the absorptive properties of the straw for providing a substrate in optimum condition for carrying out the fermentation. Thus in the acid-treating step, the portion of the straw which is not hydrolyzed retains its fibrous nature and acts as a matrix to hold water, sugars, and other soluble solids. When this mass is ammoniated in the next step, the formed ammonium sulphate is held in the fibrous matrix with the other soluble components. Thus there is made available a material in prime condition for fermentation. It contains water, mineral salts, and carbon and nitrogen sources required for growth of the microorganism. Moreover, all these components are held in the matrix of the fibrous straw material, forming a semi-solid mass so that the fermentation can be carried out in simple fashion by tumbling in the presence of air and eliminating all the elaborate equipment and controls which would be required if the substrate were a liquid.

EXAMPLES

The invention is further demonstrated by the following illustrative examples.

Annual ryegrass (*Lolium multiform Lam*) was sundried and ground to pass a 20-mesh screen. The straw (1 part) was mixed with 3 parts of 0.5 N $H_2SO_4$ and the mixture heated in a pressure cooker at 121° C. for 30 minutes.

The acid-treated straw was removed from the pressure cooker, cooled to room temperature and enough ammonium hydroxide was mixed with it to provide a pH of 4.0–4.5.

The ammoniated material was divided into three samples, and each was inoculated with 5% of its weight of a culture of a different microorganism. The microorganisms used were *Candida utilis* (NRRL Y-1084), *Pullularia pullulans* (NRRL Y-6220), and *Trichoderma viride* (OM-9123). The inoculated samples were placed in loosely-capped bottles which were secured to a device which provided continuous tumbling action to the fermenting mass. The fermentation was carried out at room temperature for 3 days. After completion of the fermentation the products were analyzed for protein content and assayed for digestibility.

Another series of runs was also carried out as described above, but with a difference in the temperature used in the acid treatment, namely, 100° C. instead of 121° C.

Digestibility

In vitro rumen digestibility was determined as follows: A 0.5 g. sample of the candidate material and 35 ml. of rumen fluid were placed in a 50-ml. screwcapped bottle. The rumen fluid was obtained from a fistulated Holstein bull, and was mixed with a mineral and buffer solution at a ratio of 1:1. The mineral and buffer solution contained 9.88 g. of $NaHCO_3$, 9.3 g. of $Na_2HPO_4 \cdot 12H_2O$, 0.47 g. of NaCl; 0.57 g. of KCl, 0.04 g. of $CaCl_2$, and 0.06 g. of $MgCl_2$ in one liter of water. The rumen fluid was gassed with $CO_2$ and warmed to 39° C. prior to inoculation with the candidate material. The mixture of the candidate material and rumen fluid was incubated for 3 days at 39° C. and then filtered through a sintered glass crucible (Pyrex, 30 ml., coarse) and the solid material on the filter dried overnight at 105° C. The weight loss was reported as percentage digestibility.

The results are summarized in the table below.

| Run | Acid treatment Temp., °C. | Fermentation, microorganism used | Digestibility % | Protein[a] % |
|---|---|---|---|---|
| 1 | 121 | C. utilis | 46.7 | 12.4 |
| 2 | 100 | do. | 42.8 | 9.3 |
| 3 | 121 | P. pullans | 44.4 | 13.9 |
| 4 | 100 | do. | — | 8.2 |
| 5 | 121 | T. viride | 43.8 | 10.9 |
| 6 | 100 | do. | 42.6 | 9.2 |
| Control[b] | — | — | 32.7 | 3.1 |

[a]Protein = Organic N × 6.25
[b]Untreated ryegrass straw

Having thus described the invention, what is claimed is:

1. A process for increasing the digestibility and protein content of straw, which consists of
   a. mixing 1 part of straw with about 2 to 4 parts of aqueous sulphuric acid having a normality of about 0.1 to 1, and holding the mixture at about 100° to 125° C. for about 30 to 60 minutes,
   b. adding to the acid-treated straw an amount of ammonia to provide a pH of about 4.0–4.5,
   c. aerobically fermenting the ammoniated acid-treated straw, which is a moist fibrous mass having a solids content of about 20–33% and a moisture content of about 80–67%, with a microorganism selected from the group consisting of *Candida utilis*, *Pullularia pullulans*, and *Trichoderma viride*, at a temperature of about 30° C. for a period of about 1 to 7 days, and
   d. drying the so-fermented product.

2. A process for increasing the digestibility and protein content of straw, which consists of
   a. mixing one part of straw with about 3 parts of aqueous sulphuric acid having a normality of about 0.5, and holding the mixture under autogenous pressure at a temperature of about 121° C. for about 30 minutes,
   b. cooling the resulting acid-treated straw to room temperature and adding thereto an amount of ammonia to provide a pH of about 4.0–4.5,
   c. inoculating the ammoniated acid-treated straw, which is a moist, fibrous, semi-solid mass having a solids content of about 25% and a moisture content of about 75%, with about 5% of a culture of a microorganism selected from the group consisting of *Candida utilis*, *Pullularia pullulans*, and *Trichoderma viride*, and aerobically fermenting the inoculated mass by tumbling it in the presence of air, said fermentation being conducted at a temperature of about 30° C. for about 1 to 7 days, and
   d. drying the so-fermented product.

3. The process of claim 2 wherein the straw is ryegrass straw.

4. The process of claim 2 wherein the microorganism is *Candida utilis*.

5. The process of claim 2 wherein the microorganism is *Pullularia pullulans*.

6. The process of claim 2 wherein the microorganism is *Trichoderma viride*.

* * * * *